United States Patent
Martino, Sr.

(10) Patent No.: US 9,354,162 B2
(45) Date of Patent: May 31, 2016

(54) METHOD USING LASER ELLIPSOMETRY FOR DETERMINING THE QUALITY OF LIQUID PRODUCT CONTAINING POLYPHENOLS

(71) Applicant: Paul Anthony Martino, Sr., Liverpool, NY (US)

(72) Inventor: Paul Anthony Martino, Sr., Liverpool, NY (US)

(*) Notice: Subject to any disclaimer, the term of this patent is extended or adjusted under 35 U.S.C. 154(b) by 0 days.

(21) Appl. No.: 14/141,602

(22) Filed: Dec. 27, 2013

(65) Prior Publication Data

US 2015/0185135 A1   Jul. 2, 2015

(51) Int. Cl.
G01J 4/00 (2006.01)
G01N 21/00 (2006.01)
G01N 21/21 (2006.01)
G01N 21/01 (2006.01)

(52) U.S. Cl.
CPC .............. G01N 21/211 (2013.01); G01N 21/01 (2013.01); G01N 2021/0106 (2013.01); G01N 2021/213 (2013.01); G01N 2201/0683 (2013.01); G01N 2201/06113 (2013.01)

(58) Field of Classification Search
CPC .......................................................... G01J 4/00
USPC ......................................................... 356/369
See application file for complete search history.

(56) References Cited

U.S. PATENT DOCUMENTS

| | | | |
|---|---|---|---|
| 2,007,716 A | 6/1934 | Green | |
| 2,137,126 A | 4/1936 | Bedford | |
| 2,127,430 A | 2/1937 | Scholes | |
| 5,798,452 A | 8/1998 | Martin | |
| 6,222,199 B1* | 4/2001 | Freeouf | 250/559.27 |
| 6,323,947 B1* | 11/2001 | Freeouf | 356/369 |
| 6,874,357 B2 | 4/2005 | Yakhno | |
| 8,263,165 B2* | 9/2012 | Sher | C12C 12/00 426/11 |

OTHER PUBLICATIONS

Tannins:definition, ansci.cornell.edu/plants.
Tannins, www.wineanorak.com/tannins.htm, Jul. 22, 2006.
Weston, L., Grape and Wine Tannins and Phenolics—Their Roles in Flavor, Quality and Human Health, Cornell University 29th Annual New York Wine Industry Workshop.

(Continued)

*Primary Examiner* — Roy M Punnoose
(74) *Attorney, Agent, or Firm* — George R. McGuire; Blaine T. Bettlinger; Bond Schoeneck & King, PLLC

(57) ABSTRACT

The objective is to develop a method for determining the quality of a liquid product containing polyphenols. The present invention is a method that is a significant improvement over existing methods that use conventional laboratory instrumentation to study the quality of liquid products. The method uses an adsorption cell with a small mirror as a reflecting surface and acts as a substrate for the adsorption of the liquid's polyphenols on its surface. The polyphenol's film thickness is measured by laser ellipsometry. Light from a monochromatic light source is reflected from the thin film of polyphenol, which changes the light's optical properties and are sensed using the principles of ellipsometry. The changes in state of polarized light are translated into graphical illustrations of measured and computed parameters that can be recognized and interpreted as distinctive properties of liquid product quality.

1 Claim, 2 Drawing Sheets

(56) References Cited

OTHER PUBLICATIONS

Dixon, G.J., Ellopsometers Measure Polarization States, Laser Focus World, Jul. 1998, pp. 107-112.

McCrackin, F., Passaglia, E., Stromberg, R., Steinberg, H., Measurement of the Thickness and Refractive Index of Very Thin Films and the Optical Properties of Surfaces by Ellipsometry, Journal of Research of the National Bureau of Standards, Jul.-Aug. 1963, vol. 67A, No. 3, pp. 363-377.

* cited by examiner

METHOD USING LASER ELLIPSOMETRY FOR DETERMINING THE QUALITY OF LIQUID PRODUCT CONTAINING POLYPHENOLS

BACKGROUND OF THE INVENTION

1. Field of the Invention

Achieving faster, better and/or more reliable methods and analyzers for determining the quality of liquids containing polyphenols is of interest in many fields. One of these fields concerns the determination of the role of polyphenols in wine quality. Polyphenols are called tannins in certain liquids, such as wine. They have the property to bind to and precipitate proteins. They are composed of a very diverse group of oligomers and polymers[1]. Current research direction involves attempts to determine the relationship between tannin structure and "mouthfeel" of red wines. Tannins contribute two characteristics to red wine: 1) astringency and 2) bitterness. Tannins are thought to cause increased friction between mouth surfaces and a sense of dryness or roughness. The term "mouthfeel" has been used to describe the sensation of wine in the mouth and it is now recognized as an important property of red wine quality. Researchers are trying to correlate mouthful properties of different tannins with their structure and composition.

2. Description of Related Art

U.S. Pat. No. 6,874,357 describes a method for determining the mechanical impedance of a test liquid drop set on the surface of a piezoelectric resonator of ultrasound frequencies which is designed for excitation of the drop during the drying-up time of the drop. The time dependence of the mechanical impedance of the drop is a sensitive parameter used to assess the quality of liquid products. This patent describes other patents (U.S. Pat. Nos. 2,137,126, 2,007,716, 2,127,430 and 5,798,452) that use similar methods for testing liquid quality and points out their shortcomings. It is recognized that the key to successful production of high quality red wine is effective tannin management. Viticulture decisions can influence the extent and nature of polyphenols that find their way into the wine. Wine makers decide on how to macerate red grapes so as to achieve the right level of polyphenol extraction. Parameters that can be manipulated include temperature of fermentation, pumping over or "punching down" the cap, choice of fermentation vessel and other variables. The presence of polyphenols or tannins in the wine product has an impact on wine flavor and overall quality. This effect has been difficult to characterize chemically and with the use of sensors. Phenols influence taste, odor, color and clarity. In the past, gas chromatography was used exclusively to measure volatile constituents in wine. Besides gas chromatography, there is High Pressure Liquid Column (HPLC) chromatography that can be used to measure monomer and polymer phenols including all major constituents in wine[3]. Polyphenols or tannins influence mouthfeel and their presence can be measured by HPLC chromatography[4]. There are other optical devices that could be used to measure the amount of polyphenols in the liquid product including photometers. Photometers (for example HANNA Instruments HI83742 Photometer) are available in the marketplace that can measure the concentration (grams/liter) of total phenols in wine. The measurement of the concentration of phenols in wine could be useful for determining the relationship of total phenols concentration with quality. However, the use of this type of photometer requires adding chemical reagents to the wine sample and waiting for a chemical reaction to occur before measuring the concentration of total phenols in wine. In addition, this photometer is limited to only wine products. Polyphenols play a role in the quality of other products. Notable sources of polyphenols include berries, tea, beer, olive oil, chocolate/cocoa, coffee, pomegranates, fruits and fruit based drinks

BRIEF SUMMARY OF THE INVENTION

In accordance with the method of the present invention, an optical apparatus and other laboratory equipment was used comprised of the following: (1) ellipsometer, (2) Abbe Refractometer, (3) pH meter, (4) adsorption cell and (5) processor (i.e., personal computer) with an ellipsometry computer program installed. Measured and computed parameters from the use of the optical apparatus and other laboratory equipment were graphically presented for determining the quality of the liquid product. Specifically, the measured and calculated parameters included the measured refractive index of the liquid under investigation, the measured pH of the liquid, and the computed polyphenol film thickness adsorbed on the reflective substrate of the adsorption cell.

In order to perform ellipsometry adsorption measurements, a light source (10) is positioned to allow a light beam (11) to pass through a polarizer (12), then through a compensator (14) and to an adsorption cell (16) containing the liquid sample under investigation. The light is reflected from a mirror reflector (17) attached to the interior bottom wall of the adsorption cell and passes through an analyzer (18) and then on to a light detector (20).

The object of the present invention is to provide an improved method of determining the quality of a liquid product. Accordingly, besides the objects and advantages discussed above, other objects and advantages of the present invention are as follows:

(a) An object of the present invention is to provide a method of determining the quality of a liquid product containing polyphenols.

(b) Another object of the present invention is to provide an analysis method for performing comparative quality analyses of different liquids containing polyphenols.

(c) Another object of the present invention is to provide a method of determining liquid product quality that can be used in a laboratory setting.

(d) Another object of the present invention is to provide a new use for ellipsometry. The above object of providing an improved method is achieved in accordance with principles of the present invention for a method of determining the film thickness of polyphenol adsorption on a reflective surface, wherein a light beam, with a pre-defined polarization, is directed to a polyphenol film adsorbed on to a solid surface, wherein the polarization of the light beam from the reflected surface is detected, wherein a change in polarization of the reflected light beam as compared to the incident beam is detected, this change being caused by adsorption of the polyphenol on to the reflected surface. The method uses ellipsometry to measure the film thickness of polyphenol adsorption on to a solid surface. Light with a specific polarization is emitted to the measurement area where it passes through the polyphenol film and is reflected off a reflective area. Part of the light is reflected, one or several times, between the surface of the film and the reflective surface. This combination causes the plane of light polarization to be changed. The magnitude of change depends on the film's refractive index.

Further objects and advantages will become apparent from a consideration of the ensuing description and drawings.

DETAILED DESCRIPTION OF THE INVENTION

There has been no attempt (to the inventor's knowledge) to use laser ellipsometery to determine the quality of liquids containing polyphenols. The present invention uses laser ellipsometry to measure the amount of polyphenol (tannin) adsorption on to the horizontal surface of the liquid's container by determining the thickness of the polyphenol film from adsorption at a solid surface. Ellipsometry is an analytical method that is well known for examining the adsorption of extremely thin films on surfaces. The method is based on an analysis of the way in which the thin film affects the polarization of a light beam. Laser ellipsometry is a sensitive method for determining optical properties of surfaces and thin films on surfaces. Linearly polarized light reflected by a thin film on a substrate is transformed into elliptically polarized beam of light with properties that are determined by the film thickness, film index of refraction, the light beam's wavelength and the angle of incidence of the light beams[5,6].

The changes in the polarization state of light when it is reflected from a thin film can be measured with the use of laser ellipsometry. Ellipsometers are scientific instruments that are readily available in the scientific marketplace. The method in the present invention is based upon the use of ellipsometry to measure film thickness of adsorbed polyphenols on solid surfaces. In the present invention, a laser beam of light with a specific polarization is emitted at the measurement surface where it passes through a thin film absorbed on the surface and is reflected off a reflective area. Part of the light is reflected off the thin film's surface and part of the light is reflected, one or several times, between the surface of the thin film and reflective surface. This combination of reflections causes the plane of light polarization to be changed. The magnitude of the change depends on the thin film's refractive index.

Figure 1:
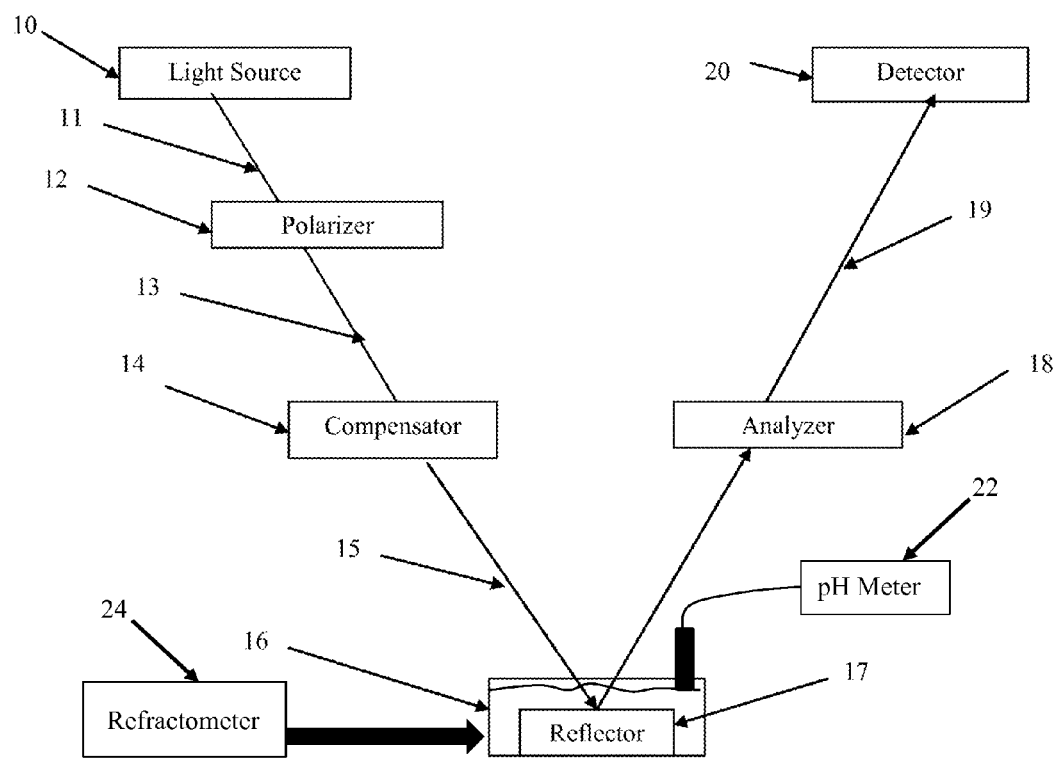
FIG. 1 shows a schematic diagram of the embodiment of an ellipsometer for determining the film thickness of polyphenol adsorbed on a solid surface."
Figure 2:
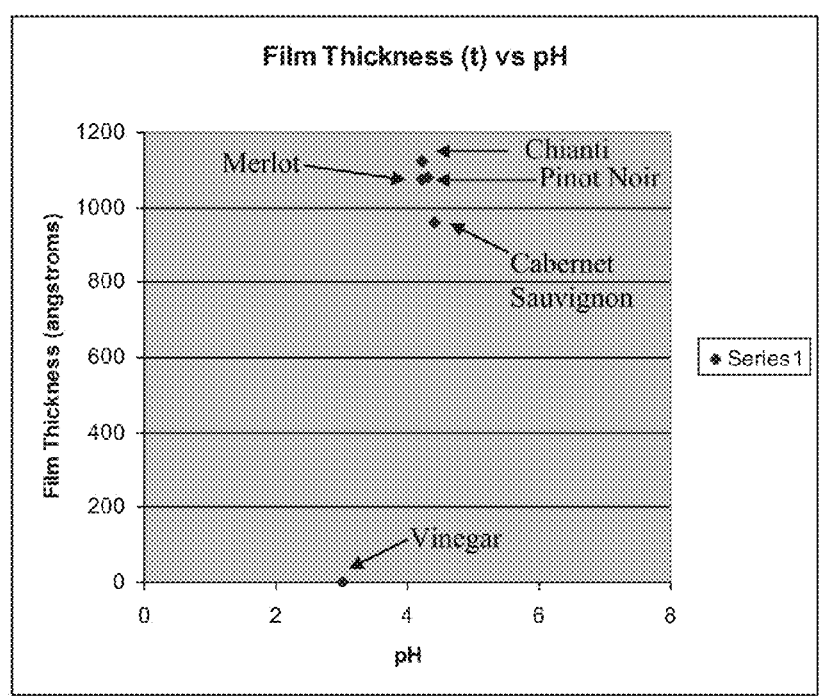
FIG. 2 shows the results of the measured and computed parameters, pH of the liquid and polyphenol film thickness. The liquid samples (various red wines) shown as a data points in the upper right hand corner of the graphical illustration represent "excellent" quality, while the liquid sample (vinegar) shown as a data point at a lower level in the graph and to the left of the wine data points represents "poor" quality.

FIG. 1 is a schematic illustration of the optical components used in ellipsometry for the present invention. In FIG. 1, a non-polarized monochromatic light source (10) provides a highly collimated light beam (11) with a small divergence of the light beam. The polarizer (12) is a transparent polarizing material that is mounted in a graduated 360-degree holder. The polarizer can be rotated about an axis parallel to the direction of the light beam and the polarizer angle can be measured. By convention, this angle is measured from the plane of incidence to the polarizer transmission axis with the positive direction counter clockwise for an observer looking into the light beam. The observed direction is opposite to the direction the light beam is travelling. The light beam becomes plane polarized light (13) after passing through the polarizer. Although not shown in FIG. 1, a telescope could be positioned between the light source and the polarizer to facilitate alignment of the light beam in the direction of the reflector.

The compensator (14) is located between the polarizer and sample under investigation. The compensator is a quarter wave plate mounted in a graduated 360-degree holder so that its plane is perpendicular to the light beam and the angle is measured from the plane of incidence to its first fast axis. The light beam becomes elliptically polarized light (15) after passing through the compensator. The compensator is normally set at an angle of plus or minus 45 degrees.

The light beam passes through a sample of liquid contained inside an adsorption cell (16). The polyphenol film under investigation is absorbed on to a reflector (17) inside the adsorption cell, which could be a mirror or reflective material with a known index of refraction. In the present invention, the reflector is a small circular mirror mounted on the interior bottom wall of an adsorption cell. The analyzer (18) is positioned after the reflector. The analyzer is a transparent polarizing material that is mounted in a 360-degree graduated holder that allows the polarized material to be rotated and the analyzer angle to be measured. The analyzer angle is the angle between the transmission axis of the analyzer and the plane of incidence as the observer is looking into the beam of light. A telescope (not shown in FIG. 1) could be positioned between the analyzer and detector (20) to aid in aligning the light beam in the direction of the detector.

The detector is positioned after the analyzer. The purpose of the detector is to determine when the reflected light beam is extinguished (19). The polarizer and analyzer angles are adjusted so that the intensity of the light reaching the detector becomes zero (the null point). The null point must be achieved in order to calculate the film thickness using ellipsometry equations in a software program installed in a processor (personal computer) associated with the ellipsometer apparatus. The detector can be a photodetector that measures light intensity of the reflected light beam or can be a reflective surface that shows the intensity of the light when detected by the human eye. In the present invention a photodetector is used in the ellipsometer to measure the intensity of the light beam. A light intensity meter display associated with the photodetector allows the user to observe the change in light intensity as it approaches zero.

When the null point measurement (zero light intensity) is achieved, the angular settings of the polarizer and analyzer are recorded and used to calculate the thickness of the thin film. Commercially available ellipsometers have software for the calculation of the film thickness based upon the measured polarizer and analyzer angular readings. Parameters used in the software to calculate the film thickness include:

1. The refractive index of the reflective substrate (i.e., mirror surface);
2. The refractive index of the polyphenol film;
3. The refractive index of the medium (i.e., liquid under measurement);
4. The angle of incidence of the light beam in degrees;
5. The orientation angle of the compensator (quarter wave plate) in degrees;
6. The wavelength of the light source in angstroms.

This invention is an optical method for studying the quality of liquid product containing polyphenols using an apparatus consisting of a laser ellipsometer with a processor (i.e., personal computer) and auxiliary laboratory equipment which includes a refractometer and pH meter. The present invention is directed to a method for studying the quality of liquid product containing polyphenols as well as determining the film thickness of polyphenol adsorption on to a solid surface. More specifically the present invention is directed to the use of an ellipsometer for the determination of film thickness from polyphenol adsorption on to a solid surface of a liquid container. The ellipsometer emits light onto a measurement surface and is directed and analyzed to identify differences in polarization of incident light and reflected light.

The present invention is considered to be an improvement over prior art because conventional methods (gas chromatography, HPLC, etc.) have not yet been proven to be reliable methods for determining the role of polyphenol's impact on liquid product quality. The present inventive method does not require adding chemical reagents to the liquid sample nor chemical reactions to occur to determine the liquid product quality. The present method of invention is not limited to a single specific liquid product. The present method of invention could be applied to any liquid product containing polyphenols. Ellipsometry is a well known analysis method for examining extremely thin films (i.e., measuring the thickness of extremely small thin films in units of angstroms (one angstrom is equal to $10^{-8}$ centimeter). Because ellipsometry has been well established as an accurate scientific method for examining thin films, a detailed description herein is not required since the method is exhaustively described elsewhere.

An important optical component for ellipsometry measurements is a source of coherent light. In the present invention, a laser was used for the light source. Note it is not necessary that a laser be used as a light source. The light source can be any type of light as long as it produces a collimated beam of light with small divergence of the light beam. In the present invention, the optical components for the ellipsometry measurements are assembled for making measurements on horizontal surfaces. The laser light beam travels downward in a vertical plane that is perpendicular to the horizontal plane and passes through an optical component called a polarizer, before passing through the compensator. The light is then reflected from the film surface and passes upward through another optical component called an analyzer before reaching the light detector. In the present invention, the polarizer is set at an angle of 45 degrees and the analyzer is rotated to remove ellipticity until the light is plane polarized and to achieve extinction of the reflected light. Other investigators do not set the polarizer at a fixed angle of 45 degrees. Instead the polarizer and analyzer angular positions are adjusted alternately until the light is extinguished as determined by the detector. Once extinction of the reflected light beam is achieved, the azimuth angles of the polarizer and analyzer are recorded for entry into the ellipsometer computer program.

Example liquids used to determine their level of quality in the present invention are:
  red wine
  red vinegar The adsorption cell in the present invention is a petri dish with a small circular mirror mounted at the center of the interior bottom wall of the cell, which faces the incident light beam.

The optical components arranged for ellipsometry measurements allow a light beam (11) from a light source (10) to pass through a polarizer (12), then through a compensator (14), reflected from the small circular mirror (17), then pass through an analyzer (18) and finally on to a light detector (20). The sequence of operations for evaluating the quality of liquid product containing polyphenols is to first measure the refractive index of the liquid using a refractometer. Next the pH of the liquid is measured with the use of a pH meter. Ellipsometry measurements are then conducted to determine the thickness of the polyphenol film adsorbed on the surface of the reflective surface within the adsorption cell.

In order to determine the refractive index of the mirror surface, ellipsometry readings are first taken without any liquid of interest in the adsorption cell (i.e., in air) or with distilled water in the adsorption cell. A refractive index of the mirror surface reported in the literature could also be used instead of the refractive index determined by ellipsometry measurements. The measured Polarizer and Analyzer readings along with the other input data required for the computer program are used to calculate the refractive index of the mirror surface in air or in distilled water. After obtaining Polarizer and Analyzer readings in air or distilled water, the transparent cell is filled with the liquid to be analyzed. Another set of Polarizer and Analyzer readings is taken with the liquid inside the adsorption cell. The computer program is used to calculate the polyphenol film thickness formed from the adsorption of polyphenol on the surface of the mirror based upon the measured Polarizer and Analyzer readings.

REFERENCES CITED

| U.S. Patent Documents | | |
|---|---|---|
| 6,874,357 | Apr. 5, 2005 | Yakhno et. al. |

OTHER PUBLICATIONS

1. Cornell University of Agriculture and Life Sciences web site (anci.cornell.edu/plants)
2. Wine Anorak web site (wineanorak.com/tannins)
3. Price, S. Developing Analytical Tools for Winemakers: Wine Phenolic Compounds and Color, 1997, $1^{st}$ International Colliquium Burgandy-California-Oregon, Dijon, France.
4. Weston, L. Grape and Wine Tannins and Phenolics-Their Roles in Flavor, Quality and Human Health, Cornell University, 1997.
5. Dixon, G. J., Ellipsometers Measure Polarization States, *Laser Focus World*, July 1998, pages 107-111.
6. McCrackin, F. L., E. Passaglia, R. R. Stromberg, and H. L. Steinberg, Measurement of the Thickness and Refractive Index of Very Thin Films and Optical Properties of Surfaces by Ellipsometry, *Journal of Research of National Bureau of Standards (A. Physics and Chem.)*, Vol. 67A, No. 14, July-Aug. 1963.

Accordingly, the reader will see that an optical method and apparatus consisting of an ellipsometer, refractometer and pH meter can be used to determine liquid product quality easily and quickly. It can be seen that the optical method with the use of polarized light is an improvement over existing methods of determining the role of polyphenols in liquid product quality. The optical method of using polarized light is a reliable method of determining the effect of polyphenols on liquid product quality. The optical method presented herein does not require the use of chemical reactions with special chemical additives in the liquid of interest to determine liquid product quality. Furthermore it can be seen that the optical method using polarized light can be an efficient method that uses the principles of ellipsometry to easily determine the quality of different types of liquid products containing polyphenols.

While the above description contains many specifics, these should not be construed as limitations on the scope of the invention, but rather as an exemplification of one preferred embodiment thereof. Many other variations are possible. For example, instead of using an ellipsometer with the arrangement of the optical components so that the light beam travels vertically downward towards the direction of a horizontal reflector, the ellipsometer components could be arranged so that the light beam travels horizontally with respect to a vertical reflector.

The geometric shape of the adsorption cell in the present invention is described as a petri dish with a circular mirror mounted on the interior bottom wall of the dish. There are other geometric variations that would be just as suitable for the adsorption cell. For example, the adsorption cell could have a triangular shape or have the shape of an octagon or some other type of polygon. In addition, the reflector and substrate for the adsorption cell is not limited to glass mirrors. Any reflecting surface, such as metal, can be used as a reflector and substrate for the polyphenol film. The optical method of the present invention is a state of the art ellipsometer, which is available in the scientific marketplace. However, instead of using a standard ellipsometer, an assembly of optical components resembling an ellipsometer could be used. Thus, the scope of this invention should be determined by the appended claims and their legal equivalents, rather than by the examples given.

REFERENCE NUMERALS IN DRAWINGS

10 light source
11 monochromatic light
12 polarizer
13 plane polarized light
14 compensator
15 elliptically polarized light
16 adsorption cell
17 reflector
18 analyzer
19 essentially zero light intensity
20 light detector

What is claimed is:

1. A method for quantifying a quality parameter of a liquid sample, the method comprising the steps of:
    measuring, with a refractometer, refractive index of the liquid sample;
    measuring, with a pH meter, pH of the liquid sample;
    illuminating, with a laser ellipsometric apparatus, the liquid sample contained in a cell having a reflective surface attached to an interior bottom wall of said cell;
    obtaining a measurement of the liquid sample with said laser ellipsometric apparatus;
    determining the polyphenol film thickness based on the refractive index of the liquid sample and the obtained measurement from the laser ellipsometric apparatus;
    determining a quality parameter of the liquid sample based on a comparison of the determined polyphenol film thickness and the measured pH; and
    tabulating and/or presenting the determined quality parameter in graphical form.

* * * * *